United States Patent
Gaudin et al.

[11] Patent Number: 5,990,076
[45] Date of Patent: Nov. 23, 1999

[54] BENZODIOXEPINONE AND ITS USE IN PERFUMERY

[75] Inventors: Jean-Marc Gaudin, Annemasse, France; Pierre-Alain Blanc, Crassier, Switzerland

[73] Assignee: Firemenich SA, Geneva, Switzerland

[21] Appl. No.: 09/136,013

[22] Filed: Aug. 19, 1998

[30] Foreign Application Priority Data

Sep. 9, 1997 [CH] Switzerland ............... 2123/97

[51] Int. Cl.⁶ .................. A61K 7/46; A61K 7/00
[52] U.S. Cl. .................. 512/1; 424/401; 512/8; 512/13; 512/15; 512/20; 512/27
[58] Field of Search ............... 512/1, 8, 13, 15, 512/20, 27; 424/401

[56] References Cited

U.S. PATENT DOCUMENTS

| | | | |
|---|---|---|---|
| 3,517,031 | 6/1970 | Beereboo et al. | 260/333 |
| 3,647,479 | 3/1972 | Beereboom et al. | 426/536 |
| 3,799,892 | 3/1974 | Berreboom et al. | 252/522 |
| 5,525,589 | 6/1996 | Etzweiler et al. | 512/23 |

*Primary Examiner*—Shelley A. Dodson
*Assistant Examiner*—Marina Lamm
*Attorney, Agent, or Firm*—Pennie & Edmonds LLP

[57] ABSTRACT

7-Propyl-2H,4H-1,5-benzodioxepin-3-one and its use as perfuming ingredient is described. The said compound develops an aldehyde-type fragrance typical of the aliphatic unsaturated aldehydes of current use in products like soaps, shampoos, detergents for textiles or for multiple purposes, but, contrary to these aldehydes, proved to be completely stable, chemically and olfactively, in aggressive media characteristic of these products.

10 Claims, No Drawings

BENZODIOXEPINONE AND ITS USE IN PERFUMERY

TECHNICAL FIELD AND PRIOR ART

The present invention relates to the field of perfumery. It relates, more particularly, to 7-propyl-2H,4H-1,5-benzodioxepin-3-one and its use as perfuming ingredient.

U.S. Pat. No. 3,799,892 describes a family of compounds related to the benzodioxepinone of the invention. Amongst the large number of compounds described in this document, there are cited in particular the compounds of formula (A)

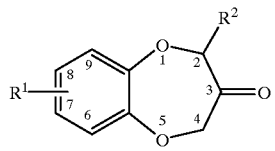

in which $R^1$ and $R^2$ represent hydrogen or an alkyl group having 1 to 4 carbon atoms, and more particularly the compounds of formula (A) carrying a methyl group in position 7 or 8 ($R^2$=H) or 2 methyl groups in positions 2 and 7 of the above-mentioned molecular structure. In spite of the description of a group of fifteen compounds of formula (A) in U.S. Pat. No. 3,799,892, this document nowhere cites the 7-propyl-2H,4H-1,5-benzodioxepin-3-one which is the object of the present invention. Even more curious is the fact that, although the object of the prior art study comprised benzoxepinones as well as benzodioxepinones, and that each of these chemical species could be substituted by a large number and variety of alkyl groups, the authors state that all the ketones described therein, generically designated as "watermelon ketones", impart to the perfumes, colognes and cosmetics into which they are incorporated fresh odors of the leaf type, reminiscent of the odor of melon, their above-mentioned perfuming effect revealing itself particularly successful in compositions having a green or violet leaf character.

DETAILED DESCRIPTION OF THE INVENTION

To our great surprise, it appears clearly that the authors of this investigation had no knowledge of the 7-propyl-2H,4H-1,5-benzodioxepin-3-one of the present invention, nor of its particular properties, which render its use in the perfume industry very important, and in particular for perfuming functional products. It is in fact well known that the media of detergent compositions, for example, are generally very aggressive against certain perfuming raw materials, the odor notes of which are, however, particularly appreciated for this type of application. One of the most obvious cases is that of the unsaturated aldehydes of current use, such as C11 aldehyde, Intreleven aldehyde (origin: International Flavor and Fragrances, Inc.), 2,6,10-trimethyl-9-undecenal, and others, which have revealed themselves completely unstable in many existing textile detergent formulations containing bleaching agents and activators like tetraacetylethylendiamine (TAED), hypohalites, in particular hypochlorite, peroxygen-derived bleaching agents, etc. Nevertheless, the olfactive qualities of these aldehydes, which are typically used for their ability to confer notes which are readily associated with the perception of the odor of clean linen, justify their widespread use, but their instability in these media continues to be a current problem, such that the search for alternative materials, from an olfactive point of view, capable of solving this problem, continues.

Now, the present invention provides a novel and advantageous solution to this exact problem. We have in fact established that the 7-propyl-2H,4H-1,5-benzodioxepin-3-one develops a strong aldehyde-type odor, very powerful and reminiscent of the odor of 2,6,10-trimethyl-9-undecenal in particular, which is however accompanied by a spicy connotation and a character which evokes the odor of clean linen drying in the sun.

Moreover, the odor of this compound is totally distinct from that of its analogues and homologues described in the patent mentioned beforehand and of which, according to our knowledge, the 7-methyl-2H,4H-1,5-benzodioxepin-3-one is the only product of the described series which has been the object of commercial exploitation (product commercialized under the name of CALONE®; origin: C.A.L. SA, Grasse, France).

Now, Calone® for example develops a flowery-green odor, with a strong ozone, marine connotation, reminiscent of the odor of oysters. Moreover, we have been able to ascertain that this marine, ozone note is quite typical of the compounds of the known series and present in various degrees of strength in the odor of the compounds of formula (A) wherein $R^2$ represents hydrogen and $R^1$ represents hydrogen or an ethyl, isopropyl, tert-butyl or 1,1-dimethylpropyl group in position 7 of the benzene ring, whereas it is totally absent from the odor of the compound which is the object of the present invention. None of these analogues, which are structurally closest to the 7-propyl-2H,4H-1,5-benzodioxepin-3-one of the invention, possesses, moreover, the strong aldehyde, spicy character which confers the whole perfumistic value to the latter in the context of the invention, making it an ingredient of choice for the perfuming of multi-purpose detergent compositions, as well as fabric softeners, in which its odor strength and substantivity provides an additional advantage. Thus, we were able to establish that, for example, textiles washed in the presence of detergents or softeners containing 7-propyl-2H,4H-1,5-benzodioxepin-3-one develop an odor of clean and fresh linen which is quite long lasting and which is particularly remarked when ironing the clothes, and this even when this ironing was done several days after the clothes had been dried.

Therefore, the invention also concerns the preferred use of the above-mentioned compound in applications such as soaps, shampoos, liquid or solid detergents for the treatment of textiles, fabric softeners, or yet detergent compositions or all-purpose household cleaners for the cleaning of dishes or various surfaces, whether they are intended for household or industrial use.

In a general manner, 7-propyl-2H,4H-1,5-benzodioxepin-3-one has revealed itself to be a perfuming ingredient which is used at its best in all consumer products in which the perfuming substances having aldehyde functions are chemically unstable. In this context, one can cite, amongst others, all the strong reducing or oxidizing media, in particular detergents and bleaching products, containing bleaching agents or activators or chlorinated products, as well as body deodorants and antiperspirants which contain for example aluminum salts. As springs out from the examples presented further on, the benzodioxepinone of the invention has revealed itself perfectly stable in these media, while its odor note lends itself particularly well to the fragrances usual in such consumer products.

The present invention therefore renders available to the perfumer a unique product with a typical aldehyde connotation which can freely be used in media in which the use of current odorant products capable of conferring said perfuming effect is often forbidden to the perfumer, or in any case rendered difficult.

Of course, its use is however not limited to the products mentioned beforehand, and this compound also lends itself to all other current uses in perfumery, namely the preparation of perfumes and colognes, the perfuming of soaps and shower gels, hygiene or hair-care products, as well as of air fresheners or yet cosmetic preparations.

In these applications, it can be used alone or in admixture with other perfuming ingredients, solvents or adjuvants of current use in perfumery. The nature and the variety of these coingredients do not require a more detailed description here, which, moreover, would not be exhaustive, and the person skilled in the art will be able to choose the latter through its general knowledge and as a function of the nature of the product to be perfumed and of the desired olfactive effect. These perfuming ingredients belong to chemical classes as varied as alcohols, aldehydes, ketones, esters, ethers, acetates, nitriles, terpene hydrocarbons, sulfur- and nitrogen-containing heterocyclic compounds, as well as essential oils of natural or synthetic origin. A large number of these ingredients is moreover listed in reference textbooks such as the book of S. Arctander, Perfume and Flavor Chemicals, 1969, Montclair, N.J., USA, or its more recent versions, or in other works of similar nature.

The proportions in which the compound according to the invention can be incorporated in the various products mentioned beforehand vary within a large range of values. These values depend on the nature of the article or products that one desires to perfume and the olfactive effect searched for, as well as on the nature of the coingredients in a given composition when the compound of the invention is used in admixture with perfuming coingredients, solvents or adjuvants of current use in the art.

As an example, there can be cited typical concentrations of the order of 0.1 to 1%, or even more, by weight of this compound relative to the weight of the perfuming composition in which it is incorporated. Far lower concentrations than those mentioned can be used when the compound is directly applied for the perfuming of the various consumer products cited beforehand.

The invention will now be described in a more detailed manner in the following examples.

EMBODIMENTS OF THE INVENTION

EXAMPLE 1

Preparation of 7-propyl-2H,4H-1,5-benzodioxepin-3-one

This compound was prepared using known reactions, starting from 97% pure 4-propyl-1,2- benzenediol. This starting product, having an odor of the copper, phenolic, slightly fatty type, was converted in an analogous way to that described in U.S. Pat. No. 3,799,892 to give a crude product which, after purification and crystallization in heptane at −20° C., gave 7-propyl-2H,4H-1,5-benzodioxepin-3-one with a purity above 99%, showing the following spectral data:

NMR($^{13}$C): 13.75(q); 24.42(t); 37.09(t); 75.49(t); 75.77 (t); 120.53(d); 120.60(d); 123.71(d); 138.71(s); 146.22(s); 147.98(s); 204.85(s) δ ppm NMR($^{1}$H): 0.93(t, J=8, 3H); 1.60(m, 2H); 2.50(t, J=6, 2H); 4.66(s, 2H); 4.70(s, 2H); 6.76(dd, J=2, J=8, 1H); 6.80(d, J=2, 1H); 6.90(d, J=8, 1H) δ ppm MS: 206(M$^+$): 177(100), 149(30), 135(10), 123(8), 105 (5), 91(10), 77(18), 65(10), 55(8), 51(10), 39(10).

EXAMPLE 2

Preparation of a Perfuming Composition for a Soap

A base perfuming composition of floral-powdery character, intended for a soap, was prepared by mixing the following ingredients:

| Ingredient | Parts by weight |
| --- | --- |
| Benzyl acetate | 80 |
| Citronellyl acetate | 50 |
| Verdyl acetate | 80 |
| Anisic aldehyde | 30 |
| 50%* Undecanal | 20 |
| 10%* Cetalox ®[1] | 20 |
| Cyclamen aldehyde | 15 |
| Dihydromyrcenol[2] | 40 |
| Habanolide ®[3] | 45 |
| Hedione ®[4] | 50 |
| Iralia ®[5] | 40 |
| Iso E Super[6] | 80 |
| Lilial ®[7] | 60 |
| Lorysia ®[8] | 220 |
| 10%* Methyl octyne carbonate | 10 |
| Polysantol ®[9] | 10 |
| Hexyl salicylate | 150 |
| Total | 1000 |

*in dipropyleneglycol (DIPG)
[1] dodecahydro-3a,6,6,9a-tetramethyl-naphtho[2,1-b]furane; origin: Firmenich SA, Geneva, Switzerland
[2] 2,6-dimethyl-7-octen-2-ol; origin: International Flavors & Fragrances, USA
[3] pentadecenolide; origin: Firmenich SA, Geneva, Switzerland
[4] methyl dihydrojasmonate; origin: Firmenich SA, Geneva, Switzerland
[5] methylionone; origin: Firmenich SA, Geneva, Switzerland
[6] origin: International Flavors & Fragrances, USA
[7] 2-methyl-3-(4-tert-butyl-1-phenyl)-propanal; origin: Givaudan-Roure, Vernier, Switzerland
[8] 4-(1,1-dimethylethyl-cyclohexanol acetate; origin: Firmenich SA, Geneva, Switzerland
[9] 3,3-dimethyl-5-(2,2,3-trimethyl-3-cyclopenten-1-yl)-4-penten-2-ol; origin: Firmenich SA, Geneva, Switzerland The addition of 1% by weight of 7-propyl-2H,4H-1,5-benzodioxepin-3-one to this base composition imparted to it a very powerful aldehydic-metallic note which slightly recalled the odorant effect that can be obtained using 2,6, 10-trimethyl-9-undecenal or 2-methylundecanal, but which, in addition, was accompanied by a pleasant floral note reminiscent of the odor of heliopropanal (origin: International Flavors & Fragrances, USA), and a spicy, pleasant undernote. Moreover, the fragrance of the composition was found to be clearly improved and its impact greatly enhanced when this novel composition was added to a soap in a concentration of 1% by weight, relative to the weight of the soap.

EXAMPLE 3

Preparation of a Perfuming Composition

A base type cologne of a floral, woody, herbaceous odor was prepared by admixing the following ingredients:

| Ingredient | Parts by weight |
| --- | --- |
| Wormwood essential oil | 200 |
| Linalyl acetate | 400 |
| 10%* Intreleven aldehyde[1] | 10 |

-continued

| Ingredient | Parts by weight |
|---|---|
| Allyl amyl glycolate | 100 |
| Artemisial essential oil | 70 |
| Ceylon cinnamon essential oil | 10 |
| Cardamon essential oil | 50 |
| Coumarin | 30 |
| α-Damascone | 20 |
| Dihydromyrcenol[2] | 900 |
| Estragol | 40 |
| Floropal ®[3] | 50 |
| 10%* Galbanum essential oil | 40 |
| Clove essential oil | 80 |
| Habanolide ®[2] | 330 |
| Hedione ®[2] | 300 |
| Iralia ®[2] | 80 |
| Isobutylquinoleine[4] | 20 |
| Lavandin essential oil | 150 |
| Mandarine essential oil | 140 |
| Crystalmoss | 100 |
| 10%* Rose oxide | 40 |
| Patchouli essential oil | 280 |
| Polysantol ®[2] | 100 |
| Sclary sage essential oil | 100 |
| 10%* Triplal ®[5] | 120 |
| Galbex ®[6] 183 | 180 |
| Total | 3990 |

*in DIPG
[1] undecenal; origin: International Flavors & Fragrances, USA
[2] see Example 2
[3] 2,4,6-trimethyl-4-phenyl-1,3-dioxane; origin: Haarman & Reimer GmbH, Germany
[4] origin: International Flavors & Fragrances, USA
[5] 2,4-dimethyl-3-cyclohexene-1-carboxaldehyde; origin: International Flavors & Fragrances, USA
[6] origin: Firmenish SA, Geneva, Switzerland The addition of 10 parts by weight of 7-propyl-2H,4H-1,5-benzodioxepin-3-one to this base composition conferred to it a modern, fresher, spicier connotation, while enhancing its fragrant impact and providing a more natural herbaceous character, which was entirely due to the typical aldehydic odor effect of the compound of the invention. The latter, moreover, completely stiffled the earthy, dirty note due to the presence of the patchouli essential oil.

EXAMPLE 4

Preparation of a Perfuming Composition for a Detergent

A base perfuming composition intended for perfuming a detergent was prepared from the following ingredients:

| Ingredient | Parts by weight |
|---|---|
| Hexylcinnamic aldehyde | 200 |
| Cetalox ®[1] | 15 |
| 10%* cis-3-Hexenol | 20 |
| Citronellyl nitrile | 5 |
| Habanolide ®[1] | 80 |
| Hedione ®[1] | 70 |
| 10%* Indol | 5 |
| Iralia ®[1] Total | 70 |
| Iso E Super[1] | 70 |
| Linalol | 80 |
| Lorysia ®[1] | 120 |
| 10%* Manzanate ®[2] | 20 |
| Mayol ®[3] | 60 |
| 10%* trans-1-(2,2,6-Trimethyl-1-cyclohexyl)-3-hexanol[4] | 20 |
| 3-Methyl-5-phenyl-1-pentanol[4] | 80 |
| Polysantol ®[1] | 15 |
| Vertofix Coeur[5] | 60 |
| Total | 980 |

*in DIPG
[1] see Example 2
[2] ethyl 2-methyl-pentanoate; origin: Quest International Fragrances
[3] 7-p-menthanol; origin: Firmenich SA, Geneva, Switzerland
[4] origin: Firmenich SA, Geneva, Switzerland
[5] origin: International Flavors & Fragrances, USA When 0.2% by weight of 7-propyl-2H,4H-1,5-benzodioxepin-3-one were added to this base composition of floral, powdery, woody character, a novel composition was obtained, the odor of which possessed the fresh, proper linen type character which up to now could only be obtained using the unsaturated aldehydes (C11 aldehyde, Intreleven aldehyde etc) typically used to this effect in classical perfumery. The thus-obtained perfume is appropriate for any use in current detergents, in particular those containing TAED in which these aldehydes proved to be completely unstable.

EXAMPLES 5 TO 20

The following articles and products mentioned below were perfumed by adding 7-propyl 2H,4H-benzodioxepin-3-one to the appropriate unperfumed bases, in the concentrations indicated:

| | Product | Concentration (% by weight) | Odor*/Aspect [3° C.] | [22° C.] | [40° C.] | Strength of the odor and coverage of the base |
|---|---|---|---|---|---|---|
| 5 | Cologne (95° alcohol) | 5.0 | S/N | S/N | S/N | VP/NC |
| 6 | Oil in water cream | 0.5 | S/N | S/N | S/N | VP/NC |
| 7 | Water in oil cream | 0.5 | S/N | S/N | S/N | P/NC |
| 8 | Shampoo | 0.5 | S/N | S/N | S/N | P/NC |
| 9 | Hair conditioner | 0.3 | S/N | S/N | S/N | VP/NC |
| 10 | Talcum powder | 0.5 | S/N | S/N | S/N | VP/NC |
| 11 | Antiperspirant (roll-on) | 0.5 | S/N | S/N | S/N | VP/NC |
| 12 | Antiperspirant (spray) | 1.0 | S/N | S/N | S/SC | P/NC |
| 13 | Deodorant (spray) | 1.3 | S/N | S/N | S/N | VP/NC |
| 14 | Hair spray | 0.4 | S/N | S/N | S/N | VP/NC |
| 15 | Soap | 1.0 | S/N | S/N | S/SC | P/NC |
| 16 | Powder detergent containing perborates | 0.2 | S | S | S | VP/NC |

-continued

| | Product | Concentration (% by weight) | Odor*/Aspect [3° C.] | [22° C.] | [40° C.] | Strength of the odor and coverage of the base |
|---|---|---|---|---|---|---|
| 17 | conc. Powder detergent containing TAED | 0.2 | S | S | S | VP/NC |
| 18 | Fabric softener | 0.2 | S | S | OM | P/NC |
| 19 | Eau de Javel | 0.2 | S | S | OM | P/NC |
| 20 | 5% aqueous HCl | 0.2 | S | S | S | VP/NC |

*S - stable = odor of the perfumed product not modified with respect to the compound
OM - odor modified
N - normal = appearance of the perfumed product unchanged with respect to the base
SC - slight coloration
VP - very powerful odor
P - powerful odor
NC - the odor of the perfuming compound covers normally that of the base The results of the tests presented in the table show that 7-propyl-2H,4H-1,5-benzodioxepin-3-one is perfectly stable in a great variety of consumer products and under the normal conditions for their use and storage, and covers effectively the odor of the base where necessary.

What we claim is:

1. Perfuming composition or perfumed product containing 7-propyl- 2H,4H-1,5-benzodioxepin-3-one as perfuming ingredient.

2. Perfumed product according to claim 2, in form of a perfume or a cologne, a cosmetic preparation, a shampoo or other hair-care product, a soap, a bath or shower gel, or an air freshener.

3. Deodorant or antiperspirant containing 7-propyl-2H, 4H-1,5-benzodioxepin-3-one as perfuming ingredient.

4. Detergent or fabric softener containing 7-propyl-2H, 4H-1,5-benzodioxepin-3-one as perfuming ingredient.

5. Detergent composition for household or industrial use, containing 7-propyl-2H,4H-1,5-benzodioxepin-3-one as perfuming ingredient.

6. Detergent composition according to claim 6, in the form of a dishwashing detergent or a cleaning product for hard surfaces.

7. A method for perfuming consumer products comprising chlorine-containing substances, bleaching agents or activators, or reducing or oxidizing agents, which method comprises adding an effective amount of 7-propyl-2H,4H-1,5-benzodioxepin-3-one to said products.

8. Consumer product containing 7-propyl-2H,4H-1,5-benzodioxepin-3-one as a perfuming ingredient.

9. Perfumed composition or perfumed product according to claim 2 further comprising a perfume as another perfuming ingredient, wherein the 7-propyl-2H,4H-1,5,-benzodioxepin-3-one and perfume are present in amounts sufficient to create an aldehyde odor accompanied by a spicy connotation.

10. Perfumed composition or perfumed product according to claim 2 wherein the 7-propyl-2H,4H- 1,5,-benzodioxepin-3-one is present in an amount of between about 0.1% to about 5% by weight of the composition or product.

* * * * *

UNITED STATES PATENT AND TRADEMARK OFFICE
CERTIFICATE OF CORRECTION

PATENT NO.   :   5,990,076

DATED   :   November 23, 1999

INVENTORS   :   Jean-Marc GAUDIN et al.

It is certified that error appears in the above-identified patent and that said Letters Patent is hereby corrected as shown below:

On the title page at [73] Assignee:  change "Firemenich SA" to --Firmenich SA--.

Column 7, line 28 (claim 2, line 1):  change "claim 2" to --claim 1--.

Column 8, line 18 (claim 6, line 1):  change "claim 6" to --claim 5--.

Column 8, line 29 (claim 9, line 2):  change "claim 2" to --claim 1--.

Column 8, line 35 (claim 10, line 2):  change "claim 2" to --claim 1--.

Signed and Sealed this

Eighteenth Day of July, 2000

Attest:

Q. TODD DICKINSON

*Attesting Officer*   *Director of Patents and Trademarks*